(12) United States Patent
Librizzi et al.

(10) Patent No.: US 7,119,059 B2
(45) Date of Patent: *Oct. 10, 2006

(54) MILD AND EFFECTIVE CLEANSING COMPOSITIONS

(75) Inventors: Joseph Librizzi, Hillsborough, NJ (US); Alison Martin, Lawrenceville, NJ (US); Irina Ganopolsky, Lawrenceville, NJ (US); Elvin R. Lukenbach, Flemington, NJ (US); Michael W. Eknoian, Warren, NJ (US)

(73) Assignee: Johnson & Johnson Consumer Companies, Inc., Skillman, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/650,495

(22) Filed: Aug. 28, 2003

(65) Prior Publication Data

US 2005/0049156 A1    Mar. 3, 2005

(51) Int. Cl.
*C11D 1/02* (2006.01)
*C11D 1/66* (2006.01)
*C11D 1/83* (2006.01)
*C11D 3/37* (2006.01)

(52) U.S. Cl. .............. 510/476; 510/123; 510/127; 510/155; 510/158; 510/159; 510/426; 510/434; 510/477; 510/492; 424/401; 424/487; 424/70.5; 424/70.16; 424/70.21; 424/70.22

(58) Field of Classification Search ................ 510/123, 510/127, 155, 158, 159, 426, 434, 476, 477, 510/492; 424/401, 487, 70.5, 70.16, 70.21, 424/70.22
See application file for complete search history.

(56) References Cited

U.S. PATENT DOCUMENTS

| 4,110,263 | A | 8/1978 | Lindemann et al. |
| 4,186,113 | A | 1/1980 | Verdicchio et al. |
| 4,215,064 | A | 7/1980 | Lindemann et al. |
| 4,233,192 | A | 11/1980 | Lindemann et al. |
| 4,263,178 | A | 4/1981 | Guth |
| 4,372,869 | A | 2/1983 | Lindemann et al. |
| 4,380,637 | A | 4/1983 | Lindemann et al. |
| 4,382,036 | A | 5/1983 | Lindemann et al. |
| 4,443,362 | A | 4/1984 | Guth et al. |
| 4,617,414 | A | 10/1986 | Lukenbach et al. |
| 4,726,915 | A | 2/1988 | Verdicchio |
| 5,373,044 | A | 12/1994 | Adams et al. |
| 5,661,189 | A | 8/1997 | Grieveson et al. |
| 5,876,705 | A | 3/1999 | Uchiyama et al. |
| 6,001,344 | A | 12/1999 | Villa et al. |
| 6,172,019 | B1 | 1/2001 | Dehan et al. |
| 6,433,061 | B1 | 8/2002 | Marchant et al. |
| 6,642,198 | B1 | 11/2003 | Pflederer et al. |
| 6,737,394 | B1 * | 5/2004 | Shana'a et al. ......... 510/417 |
| 2003/0026775 | A1 | 2/2003 | Marchesi et al. |
| 2003/0108578 | A1 | 6/2003 | Maubru |
| 2003/0147827 | A1 | 8/2003 | Decoster et al. |
| 2004/0001792 | A1 | 1/2004 | Biatry |
| 2004/0042990 | A1 | 3/2004 | Biatry |
| 2004/0047824 | A1 | 3/2004 | Biatry |
| 2004/0052739 | A1 | 3/2004 | Biatry |
| 2004/0091441 | A1 | 5/2004 | Heike et al. |
| 2004/0175342 | A1 | 9/2004 | Biatry |

FOREIGN PATENT DOCUMENTS

| DE | 100 57 925 A1 | 5/2002 |
| EP | 1 374 852 A1 | 1/2004 |
| WO | WO 03/074021 A1 | 9/2003 |
| WO | WO 03/084499 A2 | 10/2003 |
| WO | WO 04/006870 A2 | 1/2004 |

OTHER PUBLICATIONS

U.S. Appl. No. 10/650,226.
U.S. Appl. No. 10/650,573.
U.S. Appl. No. 10/650,398.
Bernhofer, et al., *Toxicology in Vitro*, 219-229 (1999).
Carbopol® Aqua SF-1 Polymer, Brilliant Gold Pearlized 2-in-1 Conditioning Shampoo Formulation, Noveon, Inc. CASF1-001, Dec. 2000.
Carbopol® Aqua SF-1 Polymer, Pearlized 2-in-1 Conditioning Shampoo formulation, Noveon, Inc., CASF1-002, Nov. 19, 2001.
Carbopol® Aqua SF-1 Polymer, Clear Shampoo Formulation, Noveon, Inc., CASF1-003, Dec. 2000.
Carbopol® Aqua SF-1 Polymer, Bath Gel with Vitamin E Moisturizing Beads Formulation, Noveon, Inc., CASF1-004, Dec. 2000.
Carbopol® Aqua SF-1 Polymer, Pearlized Mild Body Wash Formulation, Noveon, Inc., CASF1-005, Nov. 19, 2001.
Carbopol® Aqua SF-1 Polymer, Clear Bath Gel (High Betaine) Formulation, Noveon, Inc., CASF1-006, Dec. 2000.
Carbopol® Aqua SF-1 Polymer, Anti-Dandruff Shampoo Formulation, Noveon, Inc., CASF1-007, Dec. 2000.
Carbopol® Aqua SF-1 Polymer, Clear Shampoo/Bath Gel with Beads Formulation, Noveon, Inc., CASF1-008, Mar. 29, 2002.
Carbopol® Aqua SF-1 Polymer, Salicylic Acid Shampoo Formulation, Noveon, Inc., CASF1-009, Dec. 2000.

(Continued)

*Primary Examiner*—Brian P. Mruk

(57) ABSTRACT

A mild cleansing composition is disclosed. The composition includes a from about 3.5 percent to about 8.5 percent of an anionic surfactant; from about 0.1 percent to about 3 percent of a hydrophobically modified, crosslinked, anionic acrylic copolymer; and c) from about 1 percent to about 25 percent of a nonionic surfactant, wherein the weight ratio of component a) to component b) is about 1:1 to about 25:1. The composition is useful as shampoos, washes, baths, gels, lotions, creams, and the like.

14 Claims, No Drawings

OTHER PUBLICATIONS

Carbopol® Aqua SF-1 Polymer, Salicylic Acid Facial Scrub Formulation, Noveon, Inc., CASF1-010, Feb. 25, 2002.
Carbopol® Aqua SF-1 Polymer, Temporary Hair Color shampoo (Medium Brown) Formulation, Noveon, Inc., CASF1-011, Dec. 2000.
Carbopol® Aqua SF-1 Polymer, Antibacterial Liquid Hand Soap with suspended Beads Formulation, Noveon, Inc., CASF1-012, Dec. 2000.
Carbopol® Aqua SF-1 Polymer, Clear Facial Cleanser Formulation, Noveon, Inc., CASF1-013, Dec. 2000.
Carbopol® Aqua SF-1 Polymer, Clear Hydrating Body Wash with Suspended Beads Formulation, Noveon, Inc., CASF1-014, Nov. 19, 2001.
Carbopol® Aqua SF-1 Polymer, Sprayable d-Limonene Waterless Hand Cleaner Formulation, Noveon, Inc., CASF1-015, Jan. 2001.
Carbopol® Aqua SF-1 Polymer, Body Lotion Formulation, Noveon, Inc., CASF1-016, Dec. 2000.
Carbopol® Aqua SF-1 Polymer, Facial Cream Formulation, Noveon, Inc., CASF1-017, Dec. 2000.
Carbopol® Aqua SF-1 Polymer, Alpha Hydroxy Acid Cream Formulation, Noveon, Inc., CASF1-018, Dec. 2000.
Carbopol® Aqua SF-1 Polymer, Pearlized 3-in-1 Conditioning Shampoo Formulation, Noveon, Inc., CASF1-019, Nov. 19, 2001.
Carbopol® Aqua SF-1 Polymer, Clear Shampoo with Microcapsules Formulation, Noveon, Inc., CASF1-020, Dec. 2000.
Carbopol® Aqua SF-1 Polymer, Clear Baby Shampoo Formulation, Noveon, Inc., CASF1-021, Dec. 2000.
Carbopol® Aqua SF-1 Polymer, Economy Pearlized 3-in-1 Conditioning Shampoo Formulation, Noveon, Inc., CASF1-022, Jan. 2001.
Clear Conditioning Shampoo Using Ultrasil™ A-23 Silicones, Noveon, Inc., SIL-019, Dec. 12, 2002.
Clear Bath Gel (High Betaine) Using Carbopol® Aqua SF-1 Polymer, Noveon, Inc., CASF1-024EU, Feb. 10, 2003.
Clear Shampoo/Bath Gel with Beads Using Carbopol® Aqua SF-1 Polymer, Noveon, Inc., CASF1-025EU, Feb. 26, 2003.
Brilliant Gold Pearlized 2-in-1 Conditioning Shampoo Using Carbopol® Aqua SF-1 Polymer, Noveon, Inc., CASF1-026EU, Feb. 26, 2003.
Ethnic Hair Moisturizing Cream With Ultracas™ G-20, Noveon, Inc., SIL-0002, Jun. 28, 2001.
Antibacterial Hand Wash with Moisturizers Using Ultrasil™ DW-18 Silicone, Noveon, Inc., SIL-0005, Mar. 1, 2002.
Mild Conditioning Cream Shampoo, Noveon, Inc., SIL-0017, Dec. 12, 2002.
Moisturizing Shampoo for Ethnic Hair, Noveon, Inc., SIL-0020, Feb. 26, 2003.
Aveeno® Stress Relief Foaming Bath Formulation, Johnson & Johnson Consumer Companies, Inc., 2003.
Aveeno® Daily Moisturizing Foaming Bath Formulation, Johnson & Johnson Consumer Companies, Inc., 2003.
Aveeno® Positively Radiant™ Cleanser Formulation, Johnson & Johnson Consumer Companies, Inc., 2003.
Johnson's® Softwash™ Baby Shampoo Formulation, Johnson & Johnson Consumer Companies, Inc., 2002.
Johnson's® Softwash™ Baby Wash Formulation, Johnson & Johnson Consumer Companies, Inc., 2002.
Johnson's ® Soothing Skin Baby Bath Formulation, Johnson & Johnson Consumer Companies, Inc., 2001.
Invittox Protocol No. 86, "The Trans-Epithelial Permeability (TEP) Assay," (May 1994).
European Search Report dated Dec. 21, 2004 for EP appln. 04254988.1.
European Search Report dated Dec. 21, 2004 for EP appln. 04254989.9.
European Search Report dated Dec. 21, 2004 for EP appln. 04254987.3.
European Search Report dated Dec. 21, 2004 for EP appln. 04254990.7.
International Search Report dated Dec. 17, 2004 for PCT/US04/27317.
Moore, et al, "Challenging the surfactant monomer skin penetration model: Penetration of sodium dodecyl sulfate micelles into the epidermes" Journal of Cosmetic Science, Nov. 15, 2003, pp. 29-45.
Moore, et al., Penetration of mixed micelles into the epidermis: Effect of mixing sodium dodecyl sulfate with dodecyl haxa (ethylene oxide). Journal of Cosmetic Science, Nov. 15, 2002, pp. 143-159.

* cited by examiner

MILD AND EFFECTIVE CLEANSING COMPOSITIONS

BACKGROUND OF THE INVENTION

1. Field of the Invention

The present invention relates to a cleansing composition, which is mild to the skin and/or eyes with appropriate cleansing and foaming performance.

2. Description of the Prior Art

Synthetic detergents, such as cationic, anionic, amphoteric, and non-ionic surfactants, are widely used in detergent and cleansing compositions. It is desirable that such compositions possess good foam volume and stability when used in, for example, shampoos. The amount of foam generated is directly related to the perceived efficiency with which it cleans the hair. In general, the greater the volume of foam produced and the greater the stability of the foam, the more efficient the perceived cleansing action of the shampoo.

Anionic surfactants generally exhibit superior cleansing and foaming properties, and thus are incorporated into many personal cleansing compositions. However, these anionic surfactants tend to be very irritating to the skin and eyes in levels typically used, e.g., greater than about 10 weight percent. In order to produce more mild cleansing compositions, it is well-known to replace some of the anionic surfactant with other surfactants, such as nonionic and/or amphoteric surfactants. See, e.g. U.S. Pat. No. 4,726,915. Another approach to producing mild cleansing compositions is to associate the anionic surfactants with amphoteric or cationic compounds in order to yield surfactant complexes. See, e.g., U.S. Pat. Nos. 4,443,362; 4,726,915; 4,186,113; and 4,110,263. Disadvantageously, such mild cleansing compositions tend to suffer from poor foaming and cleansing performance.

It is therefore, an object of this invention to provide effective cleansing compositions that exhibit good foaming properties without compromising the mildness and safety properties of the overall cleansing composition.

SUMMARY OF THE INVENTION

The present invention relates to a personal cleansing composition comprising, consisting of, and/or consisting essentially of, based upon the total weight of the composition:

a) from about 1 percent to about 8 percent of an anionic surfactant; and
b) from about 0.1 percent to about 3 percent of a hydrophobically modified, crosslinked, anionic acrylic copolymer, wherein the weight ratio of component a) to component b) is about 1:1 to about 20:1, and wherein the composition is mild to the skin and/or eyes and is substantially free of non-ionic surfactants.

Another embodiment of the present invention relates to a personal cleansing composition comprising, consisting of, and/or consisting essentially of, based upon the total weight of the composition:

a) from about 3.5 percent to about 8.5 percent of an anionic surfactant; and
b) from about 0.1 percent to about 3 percent of a hydrophobically modified, crosslinked anionic acrylic copolymer; and
c) from about 1 percent to about 25 percent of a nonionic surfactant wherein the weight ratio of component a) to component b) composition is about 1:1 to about 25:1, and wherein the composition is mild to the skin and/or eyes.

Another embodiment of the present invention relates to a personal cleansing composition comprising, consisting of, and/or consisting essentially of, based upon the total weight of the composition:

a) from about 4 percent to about 8.5 percent of an anionic surfactant;
b) from about 0.1 percent to about 3 percent of a hydrophobically modified, anionic, acrylic crosslinked polymer; and
c) from about 1 percent to about 30 percent of an amphoteric surfactant;

wherein the weight ratio of component a) to component b) composition is 3:1 to about 40:1 and wherein the composition is mild to the skin and/or eyes and is substantially free of ocular sting.

Another embodiment of the present invention relates to a personal cleansing composition comprising, consisting of, and/or consisting essentially of, based upon the total weight of the composition:

a) from about 0.1 percent to about 12.5 percent of an anionic surfactant; and
b) from about 0.1 percent to about 8 percent of a hydrophobically modified, crosslinked anionic acrylic copolymer, wherein the weight ratio of component a) to component b) composition is about 1:1 to about 40:1, and the composition is substantially free of amphoteric surfactants and is mild to the skin.

Another embodiment of the present invention relates to a method of reducing ocular sting in a detergent composition comprised, consisting of, and/or consisting essentially of, based upon the total weight of the composition, from about 4 percent to about 8.5 percent of an anionic surfactant and from about 1 percent to about 30 percent of an amphoteric surfactant, said method comprised, consisting of, and/or consisting essentially of:

a) adding a hydrophobically modified, crosslinked anionic acrylic copolymer thereto in an amount, based upon the total weight of the composition, from greater than about 0.1 percent to about 3.0 percent, under conditions sufficient, wherein the weight ratio of anionic surfactant to hydrophobically modified, crosslinked anionic acrylic copolymer is about 3:1 to about 40:1 and the weight ratio of anionic surfactant to amphoteric surfactant is about 1:0.8 to about 1:4.

Another embodiment of the present invention relates to a method of reducing skin and/or eye irritancy in a detergent composition comprised, consisting of, and/or consisting essentially of, based upon the total weight of the composition, from about 0.1 percent to about 12.5 percent of an anionic surfactant, said method comprised, consisting of, and/or consisting essentially of:

a) adding a hydrophobically modified, crosslinked anionic acrylic copolymer thereto in an amount, based upon the total weight of the composition, from greater than about 0.1 percent to about 8 percent, under conditions sufficient, wherein the weight ratio of anionic surfactant to hydrophobically modified, crosslinked anionic acrylic copolymer is about 1:1 to about 40:1.

DETAILED DESCRIPTION OF PREFERRED EMBODIMENTS

As used herein, "copolymers" shall mean a polymer formed from two or more mer units and includes, but is not limited to terpolymers.

As used herein, compositions that are "mild to the skin" refer to compositions that have low skin irritancy properties as indicated by: a) a relatively high TEP value as determined in accordance with the TEP Test as set forth herein; and/or b) a passing score in the four screening tests (cell viability; cell lysis; and cytokine release (IL-1∝ and IL-1ra) performed in accordance with the Skin Assay Test as set forth herein.

As used herein, a composition that is "mild to the eyes" refers to compositions that possess a relatively high TEP value as determined in accordance with the TEP Test as set forth herein.

As used herein, a composition that is "substantially free of ocular sting" or "substantial lack of ocular sting" refers to compositions that possess relatively low sting values as determined in accordance with the Ocular Sting Test as set forth herein.

As used herein, the terms "substantially free of non-ionic surfactants" shall mean that the composition contains, based upon the total weight of the composition, less than about 1.0 percent, e.g., less than about 0.5 percent, or less than about 0.1 percent, or less than about 0.01 percent, or less than about 0.001 percent, of non-ionic surfactants.

As used herein, the terms "substantially free of amphoteric surfactants" shall mean that the composition contains, based upon the total weight of the composition, less than about 1.0 percent, e.g., less than about 0.5 percent, or less than about 0.1 percent, or less than about 0.01 percent, or less than about 0.001 percent, of amphoteric surfactants.

The first embodiment of the present invention is directed to a personal cleansing composition containing, based upon the total weight of the composition, a) from about 1 percent to about 8 percent, e.g. from about 2 percent to about 7 percent or from about 3 percent to about 6 percent of an anionic surfactant; and b) from about 0.1 percent to about 3 percent, e.g. from about 0.2 percent to about 2.7 percent or from about 0.3 percent to about 2.4 percent of a hydrophobically modified, crosslinked, anionic acrylic copolymer, wherein the weight ratio of component a) to component b) is about 1:1 to about 20:1, e.g. from about 1:1 to about 10:1 or from about 1:1 to about 5:1, and wherein the composition is mild to the skin and/or eyes and is substantially free of non-ionic surfactants. In embodiments wherein substantial lack of ocular sting is of concern, the composition further contains, based upon the total weight of the cleansing composition, from about 0.5 percent to about 35 percent, e.g. from about 1 percent to about 20 percent or from about 2 percent to about 20 percent, of an amphoteric surfactant, wherein the weight ratio of anionic surfactant:amphoteric surfactant is from about 1:0.8 to about 1:4, e.g., from about 1:0.9 to about 1:3 or from about 1:1 to about 1:2.

Suitable anionic surfactants include those selected from the following classes of surfactants:

an alkyl sulfate of the formula

R'—CH$_2$OSO$_3$X';

an alkyl ether sulfate of the formula

R'(OCH$_2$CH$_2$)$_v$OSO$_3$X';

an alkyl monoglyceryl ether sulfate of the formula

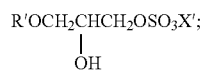

an alkyl monoglyceride sulfate of the formula

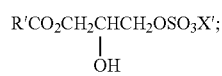

an alkyl monoglyceride sulfonate of the formula

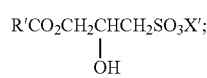

an alkyl sulfonate of the formula

an alkylaryl sulfonate of the formula

an alkyl sulfosuccinate of the formula:

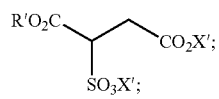

an alkyl ether sulfosuccinate of the formula:

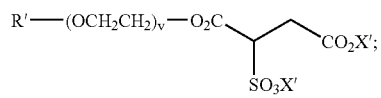

an alkyl sulfosuccinamate of the formula:

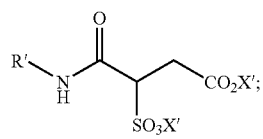

an alkyl amidosulfosuccinate of the formula

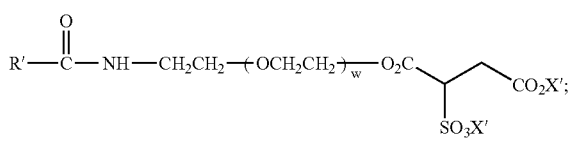

an alkyl carboxylate of the formula:

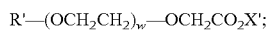

an alkyl amidoethercarboxylate of the formula:

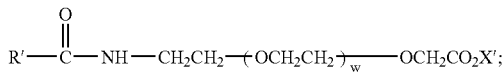

an alkyl succinate of the formula:

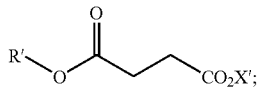

a fatty acyl sarcosinate of the formula:

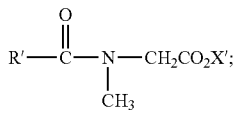

a fatty acyl amino acid of the formula:

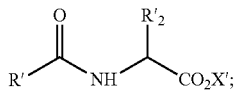

a fatty acyl taurate of the formula:

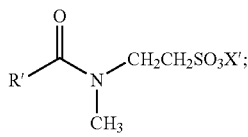

a fatty alkyl sulfoacetate of the formula:

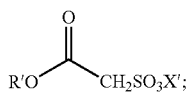

an alkyl phosphate of the formula:

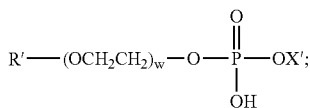

wherein
R' is an alkyl group having from about 7 to about 22, and preferably from about 7 to about 16 carbon atoms,
$R'_1$ is an alkyl group having from about 1 to about 18, and preferably from about 8 to about 14 carbon atoms,
$R'_2$ is a substituent of a natural or synthetic I-amino acid,
X' is selected from the group consisting of alkali metal ions, alkaline earth metal ions, ammonium ions, and ammonium ions substituted with from about 1 to about 3 substituents, each of the substituents may be the same or different and are selected from the group consisting of alkyl groups having from 1 to 4 carbon atoms and hydroxyalkyl groups having from about 2 to about 4 carbon atoms and
v is an integer from 1 to 6;
w is an integer from 0 to 20;

and mixtures thereof.

In one embodiment, the anionic surfactant is comprised of sodium trideceth sulfate, sodium laureth sulfate, disodium laureth sulfosuccinate, or mixtures thereof. Sodium trideceth sulfate is the sodium salt of sulfated ethoxylated tridecyl alcohol that conforms generally to the following formula, $C_{13}H_{27}(OCH_2CH_2)_nOSO_3Na$, where n has a value between 1 and 4, and is commercially available from Stepan Company of Northfield, Ill. under the tradename, "Cedapal TD-403M." Sodium laureth sulfate is available from from Albright & Wilson, Ltd. West Midlands, United Kingdom under the tradename, "Empicol 0251/70-J." Disodium laureth sulfosuccinate is available commercially from Albright & Wilson, Ltd. of West Midlands, United Kingdom under the tradename, "Empicol SDD."

Hydrophobically modified, crosslinked, anionic acrylic copolymers suitable for use in the present invention are typically in the form as random polymers, but may also exist in other forms such as block, star, graft, and the like. In one embodiment, the hydrophobically modified, crosslinked, anionic acrylic copolymer may be synthesized from at least one acidic monomer and at least one hydrophobic ethylenically unsaturated monomer. Examples of suitable acidic monomers include those ethylenically unsaturated acid monomers that may be neutralized by a base. Examples of suitable hydrophobic ethylenically unsaturated monomers include those that contain a hydrophobic chain having a carbon chain length of at least 3 carbon atoms.

In another embodiment, the hydrophobically modified, crosslinked, anionic acrylic copolymer includes those compositions derived from at least one unsaturated carboxylic acid monomer; at least one hydrophobic monomer; a hydrophobic chain transfer agent comprising alkyl mercaptans, thioesters, amino acid-mercaptan-containing compounds or peptide fragments, or combinations thereof; a cross-linking agent; and, optionally, a steric stabilizer; wherein the amount of said unsaturated carboxylic acid monomer is from about 60% to about 98% by weight based upon the total weight of said unsaturated monomers and said hydrophobic monomer, as set forth in U.S. Pat. No. 6,433,061, which is incorporated by reference herein. In one embodiment, the polymer is an acrylates copolymer that is commercially available from Noveon, Inc. under the tradename, "Carbopol Aqua SF-1."

As used herein, the term "amphoteric" shall mean: 1) molecules that contain both acidic and basic sites such as, for example, an amino acid containing both amino (basic) and acid (e.g., carboxylic acid, acidic) functional groups; or 2) zwitterionic molecules which possess both positive and negative charges within the same molecule. The charges of the latter may be either dependent on or independent of the pH of the composition. Examples of zwitterionic materials include, but are not limited to, alkyl betaines and amidoalkyl betaines. The amphoteric surfactants are disclosed herein without a counter ion. One skilled in the art would readily recognize that under the pH conditions of the compositions of the present invention, the amphoteric surfactants are either electrically neutral by virtue of having balancing positive and negative charges, or they have counter ions such as alkali metal, alkaline earth, or ammonium counter ions.

Suitable amphoteric surfactants include, but are not limited to, amphocarboxylates such as alkylamphoacetates (mono or di); alkyl betaines; amidoalkyl betaines; amidoalkyl sultaines; amphophosphates; phosphorylated imidazolines such as phosphobetaines and pyrophosphobetaines; carboxyalkyl alkyl polyamines; alkylimino-dipropionates; alkylamphoglycinates (mono or di); alkylamphoproprionates (mono or di),); N-alkyl β-aminoproprionic acids; alkylpolyamino carboxylates; and mixtures thereof.

Examples of suitable amphocarboxylate compounds include those of the formula:

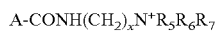
A-CONH(CH$_2$)$_x$N$^+$R$_5$R$_6$R$_7$ wherein

A is an alkyl or alkenyl group having from about 7 to about 21, e.g. from about 10 to about 16 carbon atoms;

x is an integer of from about 2 to about 6;

R$_5$ is hydrogen or a carboxyalkyl group containing from about 2 to about 3 carbon atoms;

R$_6$ is a hydroxyalkyl group containing from about 2 to about 3 carbon atoms or is a group of the formula:

R$_8$—O—(CH$_2$)$_n$CO$_2^-$ wherein

R$_8$ is an alkylene group having from about 2 to about 3 carbon atoms and n is 1 or 2; and R$_7$ is a carboxyalkyl group containing from about 2 to about 3 carbon atoms;

In one embodiment, the amphocarboxylate compound is an imidazoline surfactant, and more preferably a disodium lauroamphodiacetate, which is commercially available from Mona Chemical Company of Paterson, N.J. under the tradename, "Monateric 949J."

Examples of suitable alkyl betaines include those compounds of the formula:

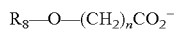
B—N$^+$R$_9$R$_{10}$(CH$_2$)$_p$CO$_2^-$ wherein

B is an alkyl or alkenyl group having from about 8 to about 22, e.g., from about 8 to about 16 carbon atoms;

R$_9$ and R$_{10}$ are each independently an alkyl or hydroxyalkyl group having from about 1 to about 4 carbon atoms; and p is 1 or 2.

A preferred betaine for use in the present invention is lauryl betaine, available commercially from Albright & Wilson, Ltd. of West Midlands, United Kingdom as "Empigen BB/J."

Examples of suitable amidoalkyl betaines include those compounds of the formula:

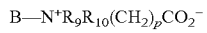
D-CO—NH(CH$_2$)$_q$—N$^+$R$_{11}$R$_{12}$(CH$_2$)$_m$CO$_2^-$ wherein D is an alkyl or alkenyl group having from about 7 to about 21, e.g. from about 7 to about 15 carbon atoms;

R$_{11}$ and R$_{12}$ are each independently an alkyl or Hydroxyalkyl group having from about 1 to about 4 carbon atoms;

q is an integer from about 2 to about 6; and m is 1 or 2.

One amidoalkyl betaine is cocamidopropyl betaine, available commercially from Goldschmidt Chemical Corporation of Hopewell, Va. under the tradename, "Tegobetaine L7."

Examples of suitable amidoalkyl sultaines include those compounds of the formula

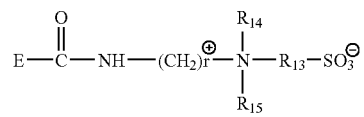

wherein

E is an alkyl or alkenyl group having from about 7 to about 21, e.g. from about 7 to about 15 carbon atoms;

R$_{14}$ and R$_{15}$ are each independently an alkyl, or hydroxyalkyl group having from about 1 to about 4 carbon atoms;

r is an integer from about 2 to about 6; and

R$_{13}$ is an alkylene or hydroxyalkylene group having from about 2 to about 3 carbon atoms;

In one embodiment, the amidoalkyl sultaine is cocamidopropyl hydroxysultaine, available commercially from Rhone-Poulenc Inc. of Cranbury, N.J. under the tradename, "Mirataine CBS."

Examples of suitable amphophosphate compounds include those of the formula:

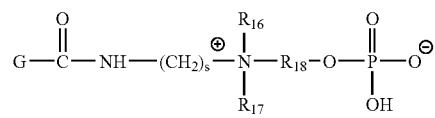

wherein

G is an alkyl or alkenyl group having about 7 to about 21, e.g. from about 7 to about 15 carbon atoms;

s is an integer from about 2 to about 6;

R$_{16}$ is hydrogen or a carboxyalkyl group containing from about 2 to about 3 carbon atoms;

R$_{17}$ is a hydroxyalkyl group containing from about 2 to about 3 carbon atoms or a group of the formula:

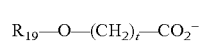
R$_{19}$—O—(CH$_2$)$_t$—CO$_2^-$ wherein

R$_{19}$ is an alkylene or hydroxyalkylene group having from about 2 to about 3 carbon atoms and t is 1 or 2; and R$_{18}$ is an alkylene or hydroxyalkylene group having from about 2 to about 3 carbon atoms.

In one embodiment, the amphophosphate compounds are sodium lauroampho PG-acetate phosphate, available commercially from Mona Industries of Paterson, N.J. under the tradename, "Monateric 1023," and those disclosed in U.S. Pat. No. 4,380,637, which is incorporated herein by reference.

Examples of suitable phosphobetaines include those compounds of the formula:

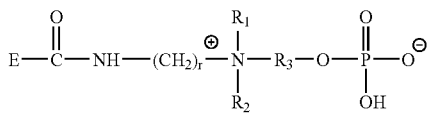

wherein E, r, $R_1$, $R_2$ and $R_3$, are as defined above. In one embodiment, the phosphobetaine compounds are those disclosed in U.S. Pat. Nos. 4,215,064, 4,617,414, and 4,233,192, which are all incorporated herein by reference.

Examples of suitable pyrophosphobetaines include those compounds of the formula:

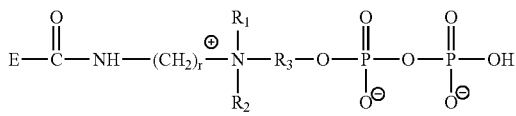

wherein E, r, $R_1$, $R_2$ and $R_3$, are as defined above. In one embodiment, the pyrophosphobetaine compounds are those disclosed in U.S. Pat. Nos. 4,382,036, 4,372,869, and 4,617,414, which are all incorporated herein by reference.

Examples of suitable carboxyalkyl alkylpolyamines include those of the formula:

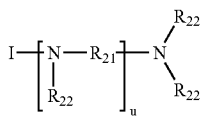

wherein
I is an alkyl or alkenyl group containing from about 8 to about 22, e.g. from about 8 to about 16 carbon atoms;
$R_{22}$ is a carboxyalkyl group having from about 2 to about 3 carbon atoms;
$R_{21}$ is an alkylene group having from about 2 to about 3 carbon atoms and
u is an integer from about 1 to about 4.

In one embodiment, the carboxyalkyl alkyl polyamine is sodium carboxymethyl coco polypropylamine, available commercially from Akzo Nobel Surface Chemistry under the tradename, "Ampholak 7CX/C."

In one embodiment, the amphoteric surfactant portion of the compositions is comprised of a mixture of amphoteric surfactants, such as amphocarboxylate and alkyl betaine, or amphocarboxylate and amidoalkyl betaine.

The second embodiment of the present invention is directed to a personal cleansing composition containing, based upon the total weight of the composition, a) from about 3.5 percent to about 8 percent, e.g. from about 4 percent to about 8 percent or from about 4.5 percent to about 8 percent of an anionic surfactant; b) from about 0.1 percent to about 3 percent, e.g., from about 0.2 percent to about 2.7 percent or from about 0.3 percent to about 2.4 percent, of a hydrophobically modified, crosslinked anionic acrylic copolymer; and c) from about 1 percent to about 25 percent, e.g. from about 1 percent to about 20 percent or from about 1 percent to about 15 percent of a nonionic surfactant, wherein the weight ratio of component a) to component b) in the composition is about 1:1 to about 40:1, e.g. from about 3:1 to about 30:1 or from about 3:1 to about 25:1 or from about 3:1 to about 20:1 or from about 3:1 to about 1:1, and wherein the composition is mild to the skin and/or eyes. In embodiments wherein substantial lack of ocular sting is also of concern, the composition further contains, based upon the total weight of the cleansing composition, from about 0.5 percent to about 35 percent, e.g. from about 1 percent to about 20 percent or from about 2 percent to about 15 percent, of an amphoteric surfactant, wherein the weight ratio of anionic surfactant:amphoteric surfactant is from about 1:0.8 to about 1:4, e.g., from about 1:0.9 to about 1:3 or from about 1:1 to about 1:2.

Examples of suitable anionic surfactants, amphoteric surfactants, and hydrophobically modified, crosslinked anionic acrylic copolymers include those set forth above.

Examples of suitable nonionic surfactants include, but are not limited to the fatty alcohol acid or amide ethoxylates, monoglyceride ethoxylates, sorbitan ester ethoxylates alkyl polyglycosides, and mixtures thereof.

One suitable nonionic surfactant is the polyoxyethylene derivatives of polyol esters, wherein the polyoxyethylene derivative of polyol ester (1) is derived from (a) a fatty acid containing from about 8 to about 22, and preferably from about 10 to about 14 carbon atoms, and (b) a polyol selected from sorbitol, sorbitan, glucose, α-methyl glucoside, polyglucose having an average of about 1 to about 3 glucose residues per molecule, glycerine, pentaerythritol and mixtures thereof, (2) contains an average of from about 10 to about 120, and preferably about 20 to about 80 oxyethylene units; and (3) has an average of about 1 to about 3 fatty acid residues per mole of polyoxyethylene derivative of polyol ester.

Examples of polyoxyethylene derivatives of polyol esters include, but are not limited to PEG-80 sorbitan laurate and Polysorbate 20. PEG-80 sorbitan laurate, which is a sorbitan monoester of lauric acid ethoxylated with an average of about 80 moles of ethylene oxide, is available commercially from ICI Surfactants of Wilmington, Del. under the tradename, "Atlas G-4280." Polysorbate 20, which is the laurate monoester of a mixture of sorbitol and sorbitol anhydrides condensed with approximately 20 moles of ethylene oxide, is available commercially from ICI Surfactants of Wilmington, Del. under the tradename "Tween 20."

Another class of suitable nonionic surfactants includes long chain alkyl glucosides or polyglucosides, which are the condensation products of (a) a long chain alcohol containing from about 6 to about 22, and preferably from about 8 to about 14 carbon atoms, with (b) glucose or a glucose-containing polymer. The alkyl gluocosides have about 1 to about 6 glucose residues per molecule of alkyl glucoside. A preferred glucoside is decyl glucoside, which is the condensation product of decyl alcohol with a glucose polymer and is available commercially from Henkel Corporation of Hoboken, N.J. under the tradename, "Plantaren 2000."

A third embodiment of the present invention is directed to a personal cleansing composition containing, based upon the total weight of the composition, a) from about 4 percent to about 8.5 percent, e.g. from about 4.5 percent to about 8 percent or from about 5 percent to about 8 percent, of an anionic surfactant; b) from about 0.1 percent to about 3 percent, e.g. from about 0.2 percent to about 2.7 percent or from about 0.3 percent to about 2.4 percent of a hydrophobically modified, anionic, acrylic crosslinked polymer; and c) from about 0.5 percent to about 35 percent, e.g. from about 1 percent to about 20 percent or from about 2 percent to about 15 percent of an amphoteric surfactant, wherein the weight ratio of anionic surfactant:amphoteric surfactant is from about 1:0.8 to about 1:4, e.g., from about 1:0.9 to about 1:3.0 or from about 1:1 to about 1.2, and wherein the weight ratio of component a) to component b) composition is about 3:1 to about 40:1, e.g. from about 3:1 to about 30:1 or from about 3:1 to about 20:1, and wherein the composition is not only mild to the skin and/or eyes, but is also substantially free of ocular sting.

Examples of suitable anionic surfactants, amphoteric surfactants, and hydrophobically modified, crosslinked anionic acrylic copolymers include those set forth above.

Another embodiment of the present invention relates to a personal cleansing composition containing, based upon the total weight of the composition, from about 0.1 percent to about 12.5 percent, e.g. from about 1 percent to about 12 percent or from about 4 percent to about 10 percent of an anionic surfactant; and b) from about 0.1 percent to about 8 percent, e.g. from about 0.2 percent to about 7 percent or from about 0.3 percent to about 6 percent, of a hydrophobically modified, crosslinked anionic acrylic copolymer, wherein the weight ratio of component a) to component b) composition is about 1:1 to about 40:1, e.g. from about 2:1 to about 30:1 or from about 3:1 to about 20:1, and the composition is substantially free of amphoteric surfactants.

Examples of suitable anionic surfactants and hydrophobically modified, crosslinked anionic acrylic copolymers include those set forth above.

Another embodiment of the present invention relates to a method of reducing ocular sting in a detergent composition containing, based upon the total weight of the composition, from about 4 percent to about 8.5 percent, e.g. from about 4.5 percent to about 8 percent or from about 5 percent to about 8 percent, of an anionic surfactant, and from about 1 percent to about 30 percent, e.g. from about 1 percent to about 20 percent or from about 2 percent to about 15 percent, of an amphoteric surfactant, by adding a hydrophobically modified, crosslinked anionic acrylic copolymer to such composition in an amount, based upon the total weight of the composition, from greater than about 0.1 percent to about 3 percent, e.g. greater than about 0.2 percent to less than about 2.7 percent or from about 0.3 percent to about 2.4 percent, under conditions sufficient, wherein the weight ratio of anionic surfactant to hydrophobically modified, crosslinked anionic acrylic copolymer is about 3:1 to about 40:1, e.g. from about 3:1 to about 30:1 or from about 3:1 to about 20:1.

Examples of suitable amphoteric surfactants and hydrophobically modified, crosslinked anionic acrylic copolymers include those set forth above.

Another embodiment of the present invention relates to a method of reducing skin and/or eye irritancy in a detergent composition containing, based upon the total weight of the composition, from about 0.1 percent to about 12.5 percent, e.g. from about 1.0 percent to about 12.0 percent or from about 4.0 percent to about 10.0 percent of an anionic surfactant, by adding a hydrophobically modified, crosslinked anionic acrylic copolymer thereto in an amount, based upon the total weight of the composition, from greater than about 0.1 percent to about 8.0 percent, e.g. greater than about 0.2 percent to about 7.0 percent or from about 0.3 percent to about 6.0 percent, under conditions sufficient, wherein the weight ratio of anionic surfactant to hydrophobically modified, crosslinked anionic acrylic copolymer is about 1:1 to about 40:1, e.g. from about 2:1 to about 30:1 or from about 3:1 to about 20:1.

Optionally, the personal cleansing compositions of this invention may also contain, based upon the total weight of the composition, from about 0.01 percent to about 1 percent, e.g. from about 0.01 percent to about 0.5 percent or from about 0.01 to about 0.2 percent, of at least one conditioning agent. Examples of suitable cationic conditioning agents nonexclusively include cationic cellulose derivatives; cationic guar derivatives; and diallyldimethylammonium chloride. Other suitable conditioning agents include those disclosed in U.S. Pat. No. 5,876,705, which is incorporated herein by reference. Surfactant soluble non-volatile silicone conditioning agents are also useful.

The cationic cellulose derivative may be a polymeric quaternary ammonium salt derived from the reaction of hydroxyethyl cellulose with a trimethylammonium substituted epoxide. The material known as Polyquaternium-10, commercially available from Amerchol Corporation of Edison, N.J. as "Polymer JR-400," is especially useful in this regard.

The cationic guar derivative may be a guar hydroxypropyltrimonium chloride, available commercially from Rhodia of Cranbury, N.J. under the tradename, "Jaguar C-17."

Other useful cationic conditioning polymers are those derived from the monomer diallyldimethylammonium chloride. The homopolymer of this monomer is Polyquaternium-6, which is available commercially form Allied Colloids of Suffolk, Va. under the tradename, "Salcare SC30." The copolymer of diallyldimethylammonium chloride with acrylamide is known as Polyquaternium-7, and is also available from Allied Colloids under the tradename "Salcare SC10."

The personal cleansing compositions of the present invention may also include one or more optional ingredients nonexclusively including a pearlescent or opacifying agent, a thickening agent, secondary conditioners, humectants, chelating agents, and additives which enhance their appearance, feel and fragrance, such as colorants, fragrances, preservatives, pH adjusting agents, and the like. The pH of the personal cleansing compositions of this invention is preferably maintained in the range of from about 5 to about 7.5, and more preferably from about 5.5 to about 7.0.

Commercially available pearlescent or opacifying agents which are capable of suspending water insoluble additives such as silicones and/or which tend to indicate to consumers that the resultant product is a conditioning shampoo are suitable for use in this invention. The pearlescent or opacifying agent may be present in an amount, based upon the total weight of the composition, of from about 1 percent to about 10 percent, e.g. from about 1.5 percent to about 7 percent or from about 2 percent to about 5 percent. Examples of suitable pearlescent or opacifying agents include, but are not limited to mono or diesters of (a) fatty acids having from about 16 to about 22 carbon atoms and (b) either ethylene or propylene glycol; mono or diesters of (a) fatty acids having from about 16 to about 22 carbon atoms (b) a polyalkylene glycol of the formula: $HO\text{-}(JO)_a\text{—}H$, wherein J is an alkylene group having from about 2 to about 3 carbon atoms; and a is 2 or 3; fatty alcohols containing from about 16 to about 22 carbon atoms; fatty esters of the formula: $KCOOCH_2L$, wherein K and L independently contain from about 15 to about 21 carbon atoms; inorganic solids insoluble in the shampoo composition, and mixtures thereof The pearlescent or opacifying agent may be introduced to the mild cleansing composition as a pre-formed, stabilized aqueous dispersion, such as that commercially available from Henkel Corporation of Hoboken, N.J. under the tradename, "Euperlan PK-3000." This material is a combination of glycol distearate (the diester of ethylene glycol and stearic acid), Laureth-4 $(CH_3(CH_2)_{10}CH_2(OCH_2CH_2)_4OH)$ and cocamidopropyl betaine and may be in a weight percent ratio of from about 25 to about 30: about 3 to about 15: about 20 to about 25, respectively.

Commercially available thickening agents, which are capable of imparting the appropriate viscosity to the personal cleansing compositions are suitable for use in this invention. If used, the thickener should be present in the shampoo compositions in an amount sufficient to raise the Brookfield viscosity of the composition to a value of between about 500 to about 10,000 centipoise. Examples of suitable thickening agents nonexclusively include: mono or diesters of 1) polyethylene glycol of formula: HO—$(CH_2CH_2O)_zH$, wherein z is an integer from about 3 to about 200; and 2) fatty acids containing from about 16 to about 22 carbon atoms; fatty acid esters of ethoxylated polyols; ethoxylated derivatives of mono and diesters of fatty acids and glycerine; hydroxyalkyl cellulose; alkyl cellulose; hydroxyalkyl alkyl cellulose; and mixtures thereof. Preferred thickeners include polyethylene glycol ester, and more preferably PEG-150 distearate which is available from the Stepan Company of Northfield, Ill. or from Comiel, S.p.A. of Bologna, Italy under the tradename, "PEG 6000 DS".

Commercially available secondary conditioners, such as volatile silicones, which impart additional attributes, such as gloss to the hair are suitable for use in this invention. In one embodiment, the volatile silicone conditioning agent has an atmospheric pressure boiling point less than about 220° C. The volatile silicone conditioner may be present in an amount of from about 0 percent to about 3 percent, e.g. from about 0.25 percent to about 2.5 percent or from about 0.5 percent to about 1.0 percent, based on the overall weight of the composition. Examples of suitable volatile silicones nonexclusively include polydimethylsiloxane, polydimethylcyclosiloxane, hexamethyidisiloxane, cyclomethicone fluids such as polydimethylcyclosiloxane available commercially from Dow Corning Corporation of Midland, Mich. under the tradename, "DC-345" and mixtures thereof, and preferably include cyclomethicone fluids.

Commercially available humectants, which are capable of providing moisturization and conditioning properties to the personal cleansing composition, are suitable for use in the present invention. The humectant may be present in an amount of from about 0 percent to about 10 percent, e.g. from about 0.5 percent to about 5 percent or from about 0.5 percent to about 3 percent, based on the overall weight of the composition. Examples of suitable humectants nonexclusively include: 1) water soluble liquid polyols selected from the group comprising glycerine, propylene glycol, hexylene glycol, butylene glycol, dipropylene glycol, and mixtures thereof; 2) polyalkylene glycol of the formula: HO—$(R"O)_b$—H, wherein R" is an alkylene group having from about 2 to about 3 carbon atoms and b is an integer of from about 2 to about 10; 3) polyethylene glycol ether of methyl glucose of formula $CH_3—C_6H_{10}O_5—(OCH_2CH_2)_c—OH$, wherein c is an integer from about 5 to about 25; 4) urea; and 5) mixtures thereof, with glycerine being the preferred humectant.

Examples of suitable chelating agents include those which are capable of protecting and preserving the compositions of this invention. Preferably, the chelating agent is ethylenediamine tetracetic acid ("EDTA"), and more preferably is tetrasodium EDTA, available commercially from Dow Chemical Company of Midland, Mich. under the tradename, "Versene 100XL" and is present in an amount, based upon the total weight of the composition, from about 0 to about 0.5 percent or from about 0.05 percent to about 0.25 percent.

Suitable preservatives include Quaternium-15, available commercially as "Dowicil 200" from the Dow Chemical Corporation of Midland, Mich., and are present in the composition in an amount, based upon the total weight of the composition, from about 0 to about 0.2 percent or from about 0.05 percent to about 0.10 percent.

The above described personal cleansing compositions may be prepared by combining the desired components in a suitable container and mixing them under ambient conditions in any conventional mixing means well known in the art, such as a mechanically stirred propeller, paddle, and the like. Although the order of mixing is not critical, it is preferable to pre-blend certain components, such as the fragrance and the nonionic surfactant before adding such components into the main mixture.

The compositions of the present invention are preferably used in personal care products such as shampoos, washes, baths, gels, lotions, creams, and the like. The compositions may also be used in conjunction with cleansing implements such as wipes, poufs, sponges, cloths, and the like, or may be impregnated therein. The compositions may also be combined with such implements for convenient sale and use in the form of a kit.

In the embodiment of the present invention wherein the detergent composition is substantially free of non-ionic surfactants, we have unexpectedly found that the addition of the hydrophobically modified, crosslinked anionic acrylic copolymer thereto not only produced a detergent composition that was mild to the skin and/or eyes, but the composition also possesses good foaming properties. Upon addition of a nonionic surfactant thereto, we have further unexpectedly found that the mildness of the resulting compositions was significantly improved. In another embodiment of the present invention wherein the detergent composition contained both an anionic surfactant and an amphoteric surfactant, we have unexpectedly found that the addition of the hydrophobically modified, crosslinked anionic acrylic copolymer thereto yields a composition having not only acceptable foaming properties, but also superior mildness and low ocular sting properties. In yet another embodiment of the present invention wherein the detergent composition contained an anionic surfactant, we have further unexpectedly found that the addition of the hydrophobically modified, crosslinked anionic acrylic copolymer thereto yielded a mild detergent without the need to additionally add amphoteric surfactants thereto and without detriment to its foaming properties.

The invention illustratively disclosed herein suitably may be practiced in the absence of any component, ingredient, or step which is not specifically disclosed herein. Several examples are set forth below to further illustrate the nature of the invention and the manner of carrying it out. However, the invention should not be considered as being limited to the details thereof.

EXAMPLES

The following tests are used in the Examples:

1) Skin Assay Test—Mildness is determined using a skin equivalent model as described by Bernhofer, et al., *Toxicology in Vitro*, 219–229 (1999), which is incorporated by reference herein. This model utilizes sequential screens for determining cell viability, cell lysis and cytokine release in order to evaluate the mildness of a surfactant system to the skin. Cell viability is determined using an alamarBlue™ assay, which is an indicator of metabolic activity. Cell lysis is detected by measuring lactate dehydrogenase (LDH) activity released from the cytosol of damaged cells. Cytokine release (both IL-1∝ and IL-1ra) is measured for those sample sets which do not exhibit loss of cell viability or cell lysis.

In general, a EpiDerm™ Epi-100 human epidermal model is obtained from MatTek Corporation (Ashland, Mass. USA) and maintained according to the manufacturers' instructions. Normal human-derived epidermal keratinocytes (NREK) are then cultured to form a multilayered differentiated model of the epidermis. After a set of NREKs is exposed in triplicate to 100 µl of a topically applied surfactant sample, it is incubated for about 1 hour. After incubation, the set is washed five times, 400 µl per wash, with phosphate buffered saline (PBS), placed onto a fresh assay media, and returned to the incubator for about 24 hours.

Cell viability of the NREKs is determined 24 and 48 hours post treatment with the alamarBlue™ assay (Alamar Biosciences. Sacramento. Calif. USA) in accordance with manufacturers' protocols and a Cytofluor II Fluorescent Plate Reader (PerSeptive Biosystems. Framingham. Mass. USA). Cell lysis is determined calorimetrically using an LDH cytotoxicity detection kit (Boehringer-Mannheim). Cytokine content is measured using human calorimetric ELISA kits for IL-1∝ (ENDOGEN. Cambridge, Mass. USA), interleukin-1 receptor antagonist (IL-1ra, R&D Systems. Minneapolis. Minn., USA), granulocyte~macrophage colony stimulating factor (GM-CSF). interleukin-6 (IL-6), interleukin-8 (IL-8). interleukin-10 (IL-b) and TNF∝ (PerSeptive Diagnostics. Cambridge, Mass. USA).

2. Ocular Sting Test: Using a double-blinded, randomized, two (2) cell study test design, one (1) drop of a sample (e.g. a 10% dilution of a cleansing composition in water) at a temperature of about 38° C. is instilled into a subject's eye. A new sterile disposable eyedropper is used for each sample and disposed of after being used on only one individual's eye. All instillations are performed either by an investigator or by a trained technician.

Within 30 seconds, or as closely as possible following instillation, the subject is asked to grade the perceived stinging sensation to the eye utilizing the following criteria:

Sting
0=Within normal limits
1=Mild, very slight
2=Moderate
3=Severe

After 15 minutes and 60 minutes post-instillation, the subject is again asked to grade the perceived stinging sensation to the eye.

3.) Trans-Epithelial Permeability Test ("TEP Test"): Irritation to the eyes expected for a given formulation is measured in accordance with the Invittox Protocol Number 86, the "Trans-epithelial Permeability (TEP) Assay" as set forth in Invittox Protocol Number 86 (May 1994). In general, the ocular irritation potential of a product can be evaluated by determining its effect on the permeability of a cell layer, as assessed by the leakage of fluorescein through the layer. Monolayers of Madin-Darby canine kidney (MDCK) cells are grown to confluence on microporous inserts in a 24-well plate containing medium or assay buffer in the lower wells. The irritation potential of a product is evaluated by measuring the damage to the permeability barrier in the cell monolayer following a 15 minute exposure to dilutions of the product. Barrier damage is assessed by the amount of sodium fluorescein that has leaked through to the lower well after 30 minutes, as determined spectrophotometrically. The fluorescein leakage is plotted against the concentration of test material to determine the $EC_{50}$ (the concentration of test material that causes 50% of maximum dye leakage, i.e., 50% damage to the permeability barrier). Higher scores are indicative of milder formulas.

Exposure of a layer of MDCK cells grown on a microporous membrane to a test sample is a model for the first event that occurs when an irritant comes in contact with the eye. In vivo, the outermost layers of the corneal epithelium form a selectively permeable barrier due to the presence of tight junctions between cells. On exposure to an irritant, the tight junctions separate, thereby removing the permeability barrier. Fluid is imbibed to the underlying layers of epithelium and to the stroma, causing the collagen lamellae to separate, resulting in opacity. The TEP assay measures the effect of an irritant on the breakdown of tight junctions between cells in a layer of MDCK cells grown on a microporous insert. Damage is evaluated spectrophotometrically, by measuring the amount of marker dye (sodium fluorescein) that leaks through the cell layer and microporous membrane to the lower well.

Examples 1–4

Preparation of Cleansing Compositions

The cleansing compositions of Examples 1 through 4 were prepared according to the materials and amounts listed in Table 1:

TABLE 1*

|  | INCI Name | 1 | 2 | 3 | 4 |
|---|---|---|---|---|---|
| Carbopol Aqua SF-1 (30%) | Acrylates Copolymer | 6.000 | 6.000 | — | — |
| Atlas G-4280 (72%) | PEG-80 Sorbitan Laurate | — | 4.580 | — | 4.580 |
| Tegobetaine L7V (30%) | Cocamidopropyl Betaine | 9.330 | 9.330 | 9.330 | 9.330 |
| Monateric 949J (30%) | Disodium Lauroamphodiacetate | 2.000 | 2.000 | 2.000 | 2.000 |
| Cedepal TD403LD (30%) | Sodium Trideceth Sulfate | 10.000 | 10.000 | 10.000 | 10.000 |
| Glycerin 917 (99%) | Glycerin | 1.900 | 1.900 | 1.900 | 1.900 |
| Polymer JR-400 | Polyquaternium-10 | 0.140 | 0.140 | 0.140 | 0.140 |
| Dowicil 200 | Quaternium-15 | 0.050 | 0.050 | 0.050 | 0.050 |
| Versene 100XL | Tetrasodium EDTA | 0.263 | 0.263 | 0.263 | 0.263 |

TABLE 1*-continued

| | INCI Name | 1 | 2 | 3 | 4 |
|---|---|---|---|---|---|
| Sodium Hydroxide solution (20%) | Sodium Hydroxide | 0.500 | 0.500 | — | — |
| Citric Acid solution (20%) | Citric Acid | — | — | 0.500 | 0.500 |
| Water | Water | qs | qs | qs | qs |

*expressed in % w/w

Preparation of Example 1: After water (50.0 parts) was added to a beaker, Carbopol Aqua SF-1 was then added thereto with mixing. The following ingredients were then added thereto independently with mixing until each respective resulting mixture was homogenous: Tegobetaine L7V, Monateric 949J, Cedepal TD403LD, Glycerin 917, Polymer JR400, Dowicil 200, and Versene 100XL. The pH of the resulting solution was then adjusted with a 20% Sodium Hydroxide solution until a final pH of about 6.3 to 6.6 was obtained. The remainder of the water was then added thereto.

Preparation of Example 2: The procedure to produce composition 1 was independently repeated, with the exception that Atlas G-4280 was added to the water/Carbopol mixture prior to the addition of the Tegobetaine L7V thereto.

Preparation of Example 3: The procedure set forth to produce composition 2 was independently repeated, with the exception that neither Carbopol nor Atlas G-4280 was added to the composition, and that the 20% Sodium Hydroxide solution was replaced with a 20% Citric Acid solution.

Preparation of Example 4: The procedure set forth to produce composition 2 was independently repeated, with the exception that the Atlas G-4280 was added to the water, and that the 20% Sodium Hydroxide solution was replaced with a 20% Citric Acid solution.

Mildness Comparison of Examples 1–4: The compositions prepared in accordance with Examples 1–4 were tested for mildness in accordance with the above TEP Test and Ocular Sting Test. Table 2 lists the TEP values and the Ocular Sting values reported for the compositions of Examples 1–4, respectively:

TABLE 2

| | Mildness Comparison | |
|---|---|---|
| Example | TEP value | % Ocular Sting Value** (Example vs Control |
| Example 1 | 4.93 ± 0.32 | 13 vs 3 |
| Example 2 | 6.23 ± 0.81 | 0 vs 0 |
| Example 3* | 4.37 ± 0.58 | 13 vs 0 |
| Example 4 | 5.29 ± 0.30 | 13 vs 7 |

*Example 3 was statistically significantly different than Example 1 at (90% CI), and was statistically significantly different than Examples 2 and 4 at (95% CI).
**With respect to ocular sting, the results of Table 2 were reported in terms of a weighted percentage of subjects who found the respective Example to be stinging to their eye versus those who perceived stinging when the control, i.e., sterile distilled water, was adminstered in their eye. In other words, the weighted percentage of subjects may be expressed in terms of:

TABLE 2-continued

| | Mildness Comparison | |
|---|---|---|
| Example | TEP value | % Ocular Sting Value** (Example vs Control |

$$\frac{X(100)}{(\text{total \#~panelists})(\text{maximum intensity score})}$$

wherein X is the sum of [(#panelists responding for a given intensity criteria)(that intensity criteria chosen)]

As demonstrated in Example 3, compositions that did not contain both a nonionic surfactant (POE 80 Sorbitan Laurate) and hydrophobically modified, crosslinked anionic acrylic copolymer (Carbopol Aqua SF-1) yielded a significantly lower TEP value than the compositions of the other three Examples. This indicated that the composition of Example 3 was comparatively the most irritating to the skin and eye tissue. Furthermore, the perceived sting value recorded for the composition of Example 3 was also comparatively higher relative to the sting values for the other compositions, which again indicated that it possessed the comparatively highest sting to the eye.

These Examples further showed that upon the addition of either a nonionic surfactant or a hydrophobically modified, crosslinked anionic acrylic copolymer to the system, (Examples 4 and 1, respectively), an increase in TEP values and an improvement in ocular sting values were noted. This indicated that the skin/eye irritation and ocular sting properties of these compositions were lowered upon the addition of either of these compounds to the system. Thus, it was unexpectedly found that a known irritation mitigant, e.g. an nonionic surfactant, may be substituted with a hydrophobically modified, crosslinked anionic acrylic copolymer in a detergent system without detriment to skin/eye irritation and ocular sting.

These Examples further showed that upon the addition of both a nonionic surfactant and a hydrophobically modified, crosslinked anionic acrylic copolymer to the system (Example 2), a significant increase in TEP values and reduction of ocular sting values were noted. This indicated that skin and eye irritation and ocular sting properties could be significantly lowered by utilizing a combination of a nonionic surfactant with a hydrophobically modified, crosslinked anionic acrylic copolymer.

Examples 5–10

Preparation of Cleansing Compositions

The cleansing compositions of Examples 5 through 10 were prepared according to the materials and amounts listed in Table 3.

TABLE 3*

|  | INCI Name | 5 | 6 | 7 | 8 | 9 | 10 |
|---|---|---|---|---|---|---|---|
| Carbopol Aqua SF-1 (30%) | Acrylates Copolymer | — | 0.900 | 2.700 | 3.600 | 4.500 | 6.000 |
| Atlas G-4280 (72%) | PEG-80 Sorbitan Laurate | 4.580 | 4.580 | 4.580 | 4.580 | 4.580 | 4.580 |
| Tegobetaine L7V (30%) | Cocamidopropyl Betaine | 11.330 | 11.330 | 11.330 | 11.330 | 11.330 | 11.330 |
| Cedepal TD403LD (30%) | Sodium Trideceth Sulfate | 20.000 | 20.000 | 20.000 | 20.000 | 20.000 | 20.000 |
| Glycerin 917 (99%) | Glycerin | 1.900 | 1.900 | 1.900 | 1.900 | 1.900 | 1.900 |
| Polymer JR-400 | Polyquaternium-10 | 0.140 | 0.140 | 0.140 | 0.140 | 0.140 | 0.140 |
| Dowicil 200 | Quaternium-15 | 0.050 | 0.050 | 0.050 | 0.050 | 0.050 | 0.050 |
| Versene 100XL | Tetrasodium EDTA | 0.263 | 0.263 | 0.263 | 0.263 | 0.263 | 0.263 |
| Water | Water | qs | qs | qs | qs | qs | qs |

*expressed in % w/w

Each of the compositions of Table 3 was independently prepared as follows:

Water (50.0 parts) was added to a beaker. For examples 6 through 10, Carbopol Aqua SF-1 was added to the water with mixing. (For Example 5, this step was omitted.) The Atlas G-4280 was then added thereto with mixing. For examples 5–10, the following ingredients were then added thereto independently with mixing until each respective resulting mixture was homogenous: Tegobetaine L7V, Cedepal TD403LD, Glycerin 917, Polymer JR400, Dowicil 200, and Versene 100XL. The pH of the resulting solution was then adjusted with either a 20% Sodium Hydroxide solution or a 20% Citric Acid solution until a final pH of about 6.3 to 6.6 was obtained. The remainder of the water was then added thereto.

Mildness Comparison of Cleansing Compositions: The compositions prepared in accordance with Examples 5–10 were then tested for mildness in accordance with the above TEP Test. Table 4 lists the TEP value of the composition of each Example:

TABLE 4

Mildness Comparison

| Example | TEP value |
|---|---|
| Example 5 | 1.46 ± 0.26 |
| Example 6 | 2.68 ± 0.28 |
| Example 7 | 2.85 ± 0.51 |
| Example 8 | 2.74 ± 0.18 |
| Example 9 | 3.34 ± 0.83 |
| Example 10 | 3.26 ± 0.39 |

As shown in Example 5, the composition containing a relatively high amount of anionic surfactant (6.0% active) without the hydrophobically modified, crosslinked anionic acrylic copolymer recorded a relatively low TEP value and thus was considered to be irritating. However, upon the addition of the hydrophobically modified, crosslinked anionic acrylic copolymer thereto as shown in Example 6, the TEP score was improved. Examples 7 to 10 further showed that as the amount of hydrophobically modified, crosslinked anionic acrylic copolymer added to the composition was increased, the TEP values for those respective compositions were generally concomitantly improved.

These Examples indicated that the presence of the hydrophobically modified, crosslinked anionic acrylic copolymer significantly improved the skin/eye mildness of the compositions, and that such mildness generally improved as the amount of the copolymer was increased. Additionally, a comparison of the composition of Example 2 and the composition of Example 10 revealed a relationship between mildness (e.g. TEP score) and the ratio of (anionic surfactant:hydrophobically modified, crosslinked anionic acrylic copolymer).

Examples 11–13

Preparation of Cleansing Compositions

The cleansing compositions of Examples 11 through 13 were prepared according to the materials and amounts listed in Table 5:

TABLE 5*

|  | INCI Name | 5/11** | 12 | 13 |
|---|---|---|---|---|
| Carbopol Aqua SF-1 (30%) | Acrylates Copolymer | — | 6.000 | 6.000 |
| Atlas G-4280 (72%) | PEG-80 Sorbitan Laurate | 4.580 | 4.580 | 4.580 |
| Tegobetaine L7V (30%) | Cocamidopropyl Betaine | 11.330 | 11.330 | 28.000 |
| Cedepal TD403LD (30%) | Sodium Trideceth Sulfate | 20.000 | 20.000 | 20.000 |
| Glycerin 917 (99%) | Glycerin | 1.900 | 1.900 | 1.900 |
| Polymer JR-400 | Polyquaternium-10 | 0.140 | 0.140 | 0.140 |
| Dowicil 200 | Quaternium-15 | 0.050 | 0.050 | 0.050 |
| Versene 100XL | Tetrasodium EDTA | 0.263 | 0.263 | 0.263 |
| Water | Water | qs | qs | qs |

*expressed in % w/w
**Example 11 is the same as Example 5

The compositions of Table 5 were prepared as follows: Water (25.0 parts) was added to a beaker. For examples 12 & 13, Carbopol Aqua SF-1 was added to the water with mixing. (For Example 11, this step was omitted.) The following ingredients were then added thereto independently with mixing until each respective resulting mixture was homogenous: Atlas G-4280, Tegobetaine L7V, Cedepal TD403LD, Glycerin 917, Polymer JR400, Dowicil 200, and Versene 100XL. The pH of the resulting solution was then adjusted with either a 20% Sodium Hydroxide solution or a 20% Citric Acid solution until a final pH of about 6.3 to 6.6 was obtained. The remainder of the water was then added thereto.

Mildness Comparison of Cleansing Compositions: The compositions prepared in accordance with Examples 11–13 were tested for mildness in accordance with the above TEP Test and Ocular Sting Test, and the results are listed below in Table 6:

TABLE 6

Mildness Comparison

| Example | TEP value | % Ocular Sting Value (Example vs Control) |
|---|---|---|
| Example 5/11** | 1.46 + 0.26 | Not Tested |
| Example 12 | 3.26 + 0.39 | 23 vs 0 |
| Example 13 | 3.02 + 0.76 | 10 vs 0 |

**Example 11 is the same as Example 5

Because the composition of Example #11, which was devoid of the hydrophobically modified, crosslinked anionic acrylic copolymer, yielded a significantly low TEP value, it was considered to be irritating and not acceptable for testing on humans; therefore, the Ocular Sting Test was not performed on that composition.

As shown in Example 12, the addition of the hydrophobically modified, crosslinked anionic acrylic copolymer to the composition contributed to the significant increase in TEP values, which indicated that the resulting composition was mild to the skin and/or eyes. However, the Ocular Sting value indicated that the composition still possessed an undesirable level of perceived sting.

Example 13 showed that upon the addition of an amphoteric surfactant to the composition of Example 12, the resulting composition was not only mild to the skin and/or eyes, but also was substantially free of ocular sting.

These Examples demonstrated that skin and eye irritation of a composition containing a relatively high amount of anionic surfactant could be reduced by the addition of the hydrophobically modified, crosslinked anionic acrylic copolymer thereto; however, the resulting composition still retained an ocular sting. These Examples further demonstrated that ocular sting effects could be reduced by the addition of an amphoteric surfactant thereto, and revealed an anionic surfactant:amphoteric surfactant ratio capable of reducing such effects.

Examples 14–19

Preparation of Cleansing Compositions

The cleansing compositions of Examples 14 through 19 were prepared according to the materials and amounts listed in Table 7:

TABLE 7*

| | INCI Name | 14 | 15 | 16 | 17 | 18 | 19** |
|---|---|---|---|---|---|---|---|
| Alcosperse 747 (40%) | Modified Polycarboxylate*** | 4.500 | — | — | — | — | — |
| PEG 8000 (100%) | PEG 8000*** | — | 1.800 | — | — | — | — |
| Polyox WSR 205 (100%) | PEG-14M*** | — | — | 1.800 | — | — | — |
| Carbopol ETD 2020 (100%) | Carbomer*** | — | — | — | 1.800 | — | — |
| Carbopol Ultrez 10 (100%) | Carbomer**** | — | — | — | — | 1.800 | — |
| Carbopol AQUA SF1 (30%) | Acrylates Copolymer | — | — | — | — | — | 6.000 |
| Tegobetaine L7V (30%) | Cocamidopropyl Betaine | 9.330 | 9.330 | 9.330 | 9.330 | 9.330 | 9.330 |
| Monateric 949J (30%) | Disodium Lauroamphodiacetate | 2.000 | 2.000 | 2.000 | 2.000 | 2.000 | 2.000 |
| Cedepal TD403LD (30%) | Sodium Trideceth Sulfate | 10.000 | 10.000 | 10.000 | 10.000 | 10.000 | 10.000 |
| Glycerin 917 (99%) | Glycerin | 1.900 | 1.900 | 1.900 | 1.900 | 1.900 | 1.900 |
| Polymer JR-400 | Polyquaternium-10 | 0.140 | 0.140 | 0.140 | 0.140 | 0.140 | 0.140 |
| Dowicil 200 | Quaternium-15 | 0.050 | 0.050 | 0.050 | 0.050 | 0.050 | 0.050 |
| Versene 100XL | Tetrasodium EDTA | 0.263 | 0.263 | 0.263 | 0.263 | 0.263 | 0.263 |
| Sodium Hydroxide solution (20%) | Sodium Hydroxide | — | — | 0.500 | 0.500 | 0.500 | 0.500 |
| Citric Acid | Citric Acid | 0.500 | 0.500 | — | — | — | — |

TABLE 7*-continued

| | INCI Name | 14 | 15 | 16 | 17 | 18 | 19** |
|---|---|---|---|---|---|---|---|
| solution (20%) | | | | | | | |
| Water | Water | qs | qs | qs | qs | qs | qs |

*expressed in % w/w
**Example 19 is the same as Example 1
***polymer is not crosslinked
****polymer is crosslinked, but not hydrophobically modified The compositions of Table 7 were prepared as follows: Water (50.0 parts) was added to a beaker. The polymer (Alcosperse 747 in Example #14, PEG 8000 in Example #15, Polyox WSR 205 in Example #16, and Carbopol ETD 2020 in Example #17) was added to the water with mixing. The following ingredients were added thereto independently with mixing until each respective resulting mixture was homogenous: Tegobetaine L7V, Monateric 949J, Cedepal TD403LD, Glycerin 917, Polymer JR400, Dowicil 200, and Versene 100XL. The pH of the resulting solution was then adjusted with either a 20% Citric Acid solution (Examples 14 & 15) or a 20% Sodium Hydroxide solution (Examples 16–19) until a final pH of about 6.3 to 6.6 was obtained. The remainder of the water was then added thereto.

Mildness Comparison of Cleansing Compositions: The compositions prepared in accordance with Examples 14–19 were tested for mildness in accordance with the above TEP Test, and the results are listed below in Table 8:

TABLE 8

Mildness Comparison

| Example | TEP value |
|---|---|
| Example 14 | 3.04 ± 0.04 |
| Example 15 | 3.64 ± 1.01 |
| Example 16 | 3.69 ± 0.98 |
| Example 17 | 4.08 ± 0.18 |
| Example 18 | Not Tested # |
| Example 19 | 4.93 ± 0.32 * |

# = Example was not stable or homogenous
* = Statistically Significantly Different (95% CI)

The composition of Example #18 (Ultrez-10), which utilized a non-hydrophobically modified acrylic polymer, was not compatible with a high electrolyte system such as that of the present cleansing composition and thus yielded an unstable, non-homogenous system that could not be tested in accordance with the TEP Test.

These Examples showed that the hydrophobically modified, crosslinked anionic acrylic copolymer provided superior irritation mitigation relative to that provided by a variety of other polymers. Statistical analysis of the data further demonstrated that the hydrophobically modified, crosslinked anionic acrylic copolymer demonstrated significantly better irritation mitigation than that of any of the other tested polymers at a 95% confidence interval.

This Example further showed that not all polymers are capable of mitigating skin/eye irritation of a cleansing surfactant composition. Accordingly, this Example suggested that both the presence of hydrophobic modification and crosslinking in the polymer contributed to the significantly reduced skin/eye irritation properties possessed by the cleansing surfactant composition.

Examples 20–23

Preparation of Cleansing Compositions

The cleansing compositions of Examples 20 through 23 were prepared according to the materials and amounts listed in Table 9:

TABLE 9*

| | INCI Name | 20 | 21 | 22 | 23 |
|---|---|---|---|---|---|
| Carbopol Aqua SF-1 (30%) | Acrylates Copolymer | 6.000 | — | 6.000 | — |
| Atlas G-4280 (72%) | PEG-80 Sorbitan Laurate | 4.580 | 4.580 | — | — |
| Tegobetaine L7V (30%) | Cocamidopropyl Betaine | 9.330 | 9.330 | — | — |
| Monateric 949J (30%) | Disodium Lauroamphodiacetate | 2.000 | 2.000 | — | — |
| Cedepal TD403LD (30%) | Sodium Trideceth Sulfate | 20.000 | 20.000 | 20.000 | 20.000 |
| Glycerin 917 (99%) | Glycerin | 1.900 | 1.900 | 1.900 | 1.900 |
| Polymer JR-400 | Polyquaternium-10 | 0.140 | 0.140 | 0.140 | 0.140 |
| Dowicil 200 | Quaternium-15 | 0.050 | 0.050 | 0.050 | 0.050 |
| Versene 100XL | Tetrasodium EDTA | 0.263 | 0.263 | 0.263 | 0.263 |
| Sodium Hydroxide solution (20%) | Sodium Hydroxide | 0.500 | — | 0.500 | — |
| Citric Acid solution (20%) | Citric Acid | — | 0.500 | — | 0.500 |
| Water | Water | 55.237 | 61.237 | 71.147 | 77.147 |

*expressed in % w/w

The compositions of Table 9 were prepared as follows: Water (50.0 parts) was added to a beaker. For examples 20 & 22 Carbopol Aqua SF-1 was added to the water with mixing. (For examples 21 & 23, this step was omitted.) For examples 20 & 21, Atlas G-4280 was then added to the water or water/Carbopol mixture. For examples 20 & 21, the following ingredients were added thereto independently with mixing until each respective resulting mixture was homogenous: Tegobetaine L7V, Monateric 949J, Cedepal TD403LD, Glycerin 917, Polymer JR400, Dowicil 200, and Versene 100XL. For examples 3 & 4, the Tegobetaine L7V and Monateric 949J were omitted. The pH of the resulting solution was then adjusted with either a 20% Sodium Hydroxide solution (Examples 20 & 22) or a 20% Citric Acid solution (Examples 21 & 23) until a final pH of about 6.3 to 6.6 was obtained. The remainder of the water was then added thereto.

Mildness Comparison of Cleansing Compositions: The compositions prepared in accordance with Examples 20–23 were tested for mildness in accordance with the above TEP Test, and the results are listed below in Table 10:

TABLE 10

Mildness Comparison

| Example | TEP value |
|---------|-----------|
| Example 20 | 1.94 ± 0.69 |
| Example 21 | 1.72 ± 0.18 |
| Example 22 | 1.19 ± 0.25 |
| Example 23 | 1.19 ± 0.14 |

The TEP value reported for the composition of Example 20 was significantly lower than the TEP values reported for similar compositions as set forth in Examples 10 and 12. Due to this inconsistency, it was unclear as to whether or not the TEP Tests for examples 20–23 were properly performed in accordance with the prescribed protocol.

Mildness Comparison of Cleansing Compositions Using Skin Assay Test: The compositions prepared in accordance with Examples 20–23 are tested for mildness in accordance with the above Skin Assay Test. This test shows that the compositions of Examples 20 and 22 pass the four screens of the Skin Assay Test and are thus considered to be mild to the skin.

We claim:

1. A personal cleansing composition comprising, based upon the total weight of the composition:
   a) from about 3.5 percent to about 8.5 percent of an anionic surfactant;
   b) from about 0.1 percent to about 3 percent of a hydrophobically modified, crosslinked, anionic acrylic copolymer derived from at least one unsaturated carboxylic acid monomer; at least one hydrophobic monomer; a hydrophobic chain transfer agent comprising alkyl mercaptans, thioesters, amino acid-mercaptan-containing compounds or peptide fragments, or combinations thereof; a cross-linking agent; and, optionally, a steric stabilizer; wherein the amount of said unsaturated carboxylic acid monomer is from about 60% to about 98% by weight based upon the total weight of said unsaturated monomers and said hydrophobic monomer; and
   c) from about 3 percent to about 25 percent of a nonionic surfactant,
   wherein the weight ratio of component a) to component b) is about 1:1 to about 25:1, and
   wherein the composition is mild to the skin and/or eyes.

2. The composition of claim 1, wherein the weight ratio of component a) to component b) is about 1:1 to about 20:1.

3. The composition of claim 1, wherein the anionic surfactant is selected from the group consisting of alkyl sulfates, alkyl ether sulfates, sulfosuccinates, isethionates, acyl amides, alkyl ether carboxylates, alkyl phosphates, and mixtures thereof.

4. The composition of claim 1, wherein the anionic surfactant is comprised of at least one of the following: alkyl ether sulfates or alkyl ether carboxylates.

5. The composition of claim 1, wherein the hydrophobically modified, crosslinked, anionic acrylic copolymer is comprised of at least one acidic monomer and at least one hydrophobic ethylenically unsaturated monomer.

6. The composition of claim 5, wherein the at least one acidic monomer is an ethylenically unsaturated acid monomer capable of neutralization with a base, and the at least one hydrophobic ethylenically unsaturated monomer is comprised of a hydrophobic carbon chain having at least three carbon atoms.

7. The composition of claim 1 further comprising, based upon the total weight of the composition, from about 1 percent to about 30 percent of an amphoteric surfactant, wherein the composition is substantially free of ocular sting.

8. The composition of claim 7, wherein the weight ratio of the anionic surfactant:amphoteric surfactant is from about 1:0.8 to about 1:4.

9. The composition of claim 7, wherein the amphoteric surfactant is selected from the group consisting of alkylimino-diproprionates, alkylamphoglycinates (mono or di), alkylamphoproprionates (mono or di), alkylamphoacetates (mono or di), N-alkyl β-aminoproprionic acids, alkylpolyamino carboxylates, phosphorylated imidazolmes, alkyl betaines, alkylamido betaines, alkyl sultaines, alkylamido sultaines, and mixtures thereof.

10. The composition of claim 1, wherein the nonionic surfactant is selected from the group consisting of fatty alcohol acid ethoxylates, fatty alcohol amide ethoxylates, monoglyceride ethoxylates, sorbitan ester ethoxylates, alkyl polyglycosides, and mixtures thereof.

11. The composition of claim 1, wherein the nonionic surfactant is a sorbitan ester ethoxylate.

12. A personal cleansing composition comprising, based upon the total weight of the composition:
   a) from about 3.5 percent to about 8.5 percent of an anionic surfactant selected from the group consisting of alkyl ether sulfates, alkyl ether carboxylates, and mixtures thereof;
   a) from about 0.1 percent to about 3 percent of a hydrophobically modified, crosslinked, anionic acrylic copolymer that is derived from at least one unsaturated carboxylic acid monomer; at least one hydrophobic monomer; a hydrophobic chain transfer agent comprising alkyl mercaptans, thioesters, amino acid-mercaptan-containing compounds or peptide fragments, or combinations thereof; a cross-linking agent; and, optionally, a steric stabilizer; wherein the amount of said unsaturated carboxylic acid monomer is from about 60% to about 98% by weight based upon the total weight of said unsaturated monomers and said hydrophobic monomer; and
   c) from about about 3 percent to about 25 percent of a nonionic surfactant selected from the group consisting of fatty alcohol amide ethoxylates, monoglyceride ethoxylates, sorbitan ester ethoxylates, alkyl polyglycosides and mixtures thereof;

wherein the weight ratio of component a) to component b) is about 1:1 to about 25:1 and wherein the composition is mild to the skin.

13. The composition of claim 12 further comprising, based upon the total weight of the composition, from about 1 percent to about 30 percent of an amphoteric surfactant, wherein the composition is substantially free of ocular sting.

14. The composition of claim 13, wherein the weight ratio of the anionic surfactant: amphoteric surfactant is from about 1:0.8 to about 1:4.

* * * * *